(12) United States Patent
Reeves et al.

(10) Patent No.: US 8,728,016 B2
(45) Date of Patent: May 20, 2014

(54) METHOD AND SYSTEM FOR TREATING PERSON SUFFERING FROM A CIRCULATORY DISORDER

(75) Inventors: Jonathan W. Reeves, Coral Springs, FL (US); William H. Reeves, Coral Springs, FL (US)

(73) Assignee: Quiecor Heart Treatment Centers of America, Crown Point, IN (US)

( * ) Notice: Subject to any disclaimer, the term of this patent is extended or adjusted under 35 U.S.C. 154(b) by 1264 days.

(21) Appl. No.: 11/857,821

(22) Filed: Sep. 19, 2007

(65) Prior Publication Data
US 2009/0076423 A1  Mar. 19, 2009

(51) Int. Cl.
*A61H 9/00* (2006.01)
(52) U.S. Cl.
USPC ............................................ 601/150; 601/152
(58) Field of Classification Search
USPC ............ 601/148, 149, 150, 151, 152; 602/13; 128/DIG. 20
See application file for complete search history.

(56) References Cited

U.S. PATENT DOCUMENTS

| 5,263,473 | A | * | 11/1993 | McWhorter | 601/152 |
| 5,443,440 | A | | 8/1995 | Tumey et al. | |
| 5,671,751 | A | | 9/1997 | Tumey et al. | |
| 5,840,049 | A | | 11/1998 | Tumey et al. | |
| 6,255,296 | B1 | | 7/2001 | Daniels | |
| 2003/0233061 | A1 | * | 12/2003 | Hui | 601/152 |

* cited by examiner

*Primary Examiner* — Quang D Thanh
(74) *Attorney, Agent, or Firm* — R. William Graham

(57) ABSTRACT

A method for therapeutically affecting the circulation of blood in a person in combination with or with medication to treat a medical condition includes the steps of administering a composition for treating a circulatory condition, providing a source of high pressure air in fluid communication with a plurality of air pressure actuated valves, each of the valves mounted on, and in fluid communication with, an inflatable bladder disposed within a cuff removably attached about at least one of the feet, calves, thighs, buttocks of the person; providing a source of low pressure air in fluid communication with said plurality of valves, wherein a constant pressure is exerted against said valves; and controlling inflation of said bladders in a predetermined sequence, magnitude of inflation pressure and period of time during a cardiac cycle of the person and as a function of said person's physiological reaction to said composition.

6 Claims, 2 Drawing Sheets

METHOD AND SYSTEM FOR TREATING PERSON SUFFERING FROM A CIRCULATORY DISORDER

FIELD OF INVENTION

The present invention is relates to advancements in circulatory therapy and benefits derived therefrom. More particularly, the invention relates to a method and system for treating persons suffering from circulatory disorders.

BACKGROUND OF THE INVENTION

One method of treating circulatory disorders has been to provide pumping assistance devices attempt to provide a non-invasive procedure for safely and effectively applying pressure to specific parts of the body. External counter pulsation devices or "ECP" devices were introduced as non-invasive circulatory assistance devices by moving blood from the extremities (legs and buttocks) up to the heart to treat angina pectoris, acute myocardial infarctions (heart attacks) and cardiogenic shock. The early ECP devices employed a liquid, typically water, to compress the extremities. Later ECP devices employed air to compress the extremities, which avoided the need to heat the water to body temperature and the risk of an electrical shock if a balloon or bladder containing the water were to leak or burst, such early ECP devices are disclosed in U.S. Pat. Nos. 3,288,132, 3,303,841, 3,403,673, 3,734,087, 3,835,845, 3,654,919, 3,866,604 and 3,388,919. Such devices are seen in FIG. 1 and show the four steps in compression. Current ECP devices typically include bladders disposed in pockets within each of two pairs of cuffs, which are fastened about the calves and thighs of a person, and two bladders contained in a single cuff which is fastened about his or her buttocks as shown in FIG. 1.

A controller operates the actuation of a plurality of valves, which valves are mounted in communication with a plurality of individual inflatable cuffs encasing the calves, thighs, and buttocks in any desired sequence towards the heart during diastole or systole, at desired times during the cardiac. A cycle of selected duration and pressures is employed for treating a variety of cardiac and non-cardiac circulatory conditions.

Another method of treating circulatory and related illness is the use of compositions which can include various drug and/or nutrients and micronutrients to improve symptoms or outcomes in chronic illness. Limited data on the actions of individual agents both in-vitro, in-vivo or in animal studies exist as to such nutrient treatments.

Unfortunately, treatments of disease processes tend to revert to the observable physiologic changes back toward a normalized condition similar to the observable, original homeostatic condition. Correction of these end-effects usually leaves the underlying molecular rearrangements responsible for the physiologic change unaffected. Treatment of vasoconstriction for example, uses vasodilators leaving the original molecular cause of the vasoconstriction untreated. The untreated molecular rearrangement processes responsible for the vasoconstriction continue unabated with resulting molecular effects which are now known to include transcriptional processes, calcium release, mitogenic effects, smooth muscle hypertrophy, autocrine and paracrine effects, and extracellular matrix accumulation of peptides all of which are both catalytic and space occupying properties.

Accumulative research evidence over the past decades indicates that molecular actions in cellular physiology are all pleuripotential, sensitive in their context sensitive as well as modifiable by numerous concurrent molecular processes. The order and organization of molecular processes in cells is highly regulated by concurrent reactions and activities in the contiguous milieu of reactants. Phosphorylation-dephosphorylation regulated processes, redox paired reactions, calcium release calmodulin activated enzyme reactions with a host of signaling transcription processes remaining tightly regulated by concurrent reaction pathways with interregulated functions.

There is an understanding that the endothelial inner lining layer of the circulatory system and other parts of the body play a major role in health and disease through responses to shear stress from circulating fluids flowing across it or pulsating upon it. The recognition that vascular endothelium is a highly active metabolic organ came with the discovery that it actively liberated nitric oxide (i.e., a mediator, a powerful relaxant of vascular smooth muscle as a function of shear stress and pulse frequency across the endothelial surface). There are known beneficial effects of provided by mediators, but there has yet to be a highly suitable means for obtaining a desired balance in the vascular system. Attempts to directly administer nitric oxide do not appear to result in a highly useful mediator due to competing molecular reactions potential toxicity. Thus, efforts to find ways to naturally release mediators into the vascular system appear to be the most feasible solution. Compounds such as nitroglycerin and other organic nitrate compounds release nitric oxide through enzymatic degradation and act directly on vascular smooth muscle to cause vasodilation. These compounds are designated endothelium independent vasodilators since they relax vascular smooth muscle even though vascular endothelium may be dysfunctional or destroyed at a given site of action. Nitric oxide donors raise a number of issues for competing metabolic events.

In addition, the present invention provides for a treatment addressing control of high concentrations of C-reactive protein (CRP) which can produce the following cascade of pathophysiological events leading toward the development of cornary vascular disease. CRP is thought to: promote monocyte chemotaxis, facilitates low-density lipoprotein uptake by macrophages in vitro; increase angiotensin type I receptor numbers and angiotensin type I receptor mediated reactive oxygen species formation, in vascular smooth muscle cells; activate stress-activated protein kinases p38 kinase and c-Jun N-terminal kinase (JNK); facilitate the release of plasminogen activator inhibitor- and endothelin-1, increase the expression of cell adhesion molecules, reduce NO bioavailability and provides the mechanism responsible for the reduced NO bioavailability in increased vascular oxidative stress; increase the production of superoxide, an NO scavenger, in cultured human aortic endothelial cells; increase oxidative stress and reduce NO bioavailability in the systemic circulation of patients with coronary artery disease; directly influence NO-mediated function by increasing oxidative stress in the coronary circulation since coronary arterioles are the predominant vessels regulating blood flow in the heart; CRP at concentrations known to predict future vascular events, weakens the antioxidant defenses of endothelial progenitor cells, and promotes early senescence through telomerase; and CRP treated cultured cells causes a significant increase in vascular NADPH oxidase activity. NADPH oxidase is a major source of agonist-induced superoxide production in vascular cells.

The prior art provided treatments for such circulatory disorders with some success. However, there remains a need to improve upon the art. The present invention provides an enhanced system for treating circulatory systems.

SUMMARY OF THE INVENTION

It is an object to improve treatment of circulatory and related problems.

It is an object to provide a method of treating employing improved pumping assistant device and composition for use therewith.

Accordingly, the instant invention provides for a system and method of treating circulatory disorders. The system includes a pumping assistant device having pressure applicators fastened about the feet, calves and thighs of a person and which are connected to a pneumatic device that can be controlled by a microprocessor. In addition, there is provided an administration of compositions which either directly or indirectly induce mediators for therapeutically treating the circulatory system. The microprocessor is operably associated with sensors sensing fluid dynamics within the circulatory system. Further, the microprocessor is operably associated with software residing on memory which performs intelligent alterations of the pumping assistant device as a function of the effect of administration of the compositions.

The present invention is believed to improve on prior circulatory treatments which neglect combining a complete and dynamic pumping assistant device with administration of compositions which can increase the effect of mediators, such as nitric oxide production in the circulatory system.

It is also the object of the present invention to provide a composition comprised of unfractionated Heparin, L-arginine, L-arginine's co-factor amino acids (L-Citrulline, L-Norvaline L-Orthithine and Nicotinamide Adenine Dinucleotide (NADH), as well as independent free radical scavenger ascorbic acid, and the superoxide scavengers (4-hyroxy-2,2,26,6-tetramethylpiperidine-N-oxyl) Tempol, and Hydroxytyrosol, Apocynin (methoxy-substrated catechol) and folic acid, or physiologically acceptable salts or equivalents and functional analogs or physiologically acceptable salts thereof in an amount which:

is directed to preventing and minimizing dysfunctional atomic and molecular interactions within human cellular environments and membranes, such interactions being associated with cardiovascular disease or disorders, by co-administration of said composition, in which components of the endothelium are stimulated to therapeutically modulate adverse molecular reactions associated with cardiovascular disease or dysfunction;

to retard adverse consequences of free radicals generated in human cellular domains relating to cardiovascular disease or disorders;

to trigger an endogenous heparin production cycle within human cellular environments;

to decrease thrombogenicity, repair cellular processes, and improve blood flow properties that are associated with thrombosis and hypoxia within a human cellular environment;

to avoid known side effects such as thrombocytopenia and bleeding attendant with the administration of heparin alone;

to treat and prevent cardiovascular disease or disorders;

to block the cardiovascular physiological processes, such as the regulation of vascular tone and oxygen sensing as well as pathophysiological processes such as endothelial dysfunction, inflammation, hypertrophy, apoptosis, migration, angiogenesis, and vascular and cardiac remodeling caused by a family of NADPH oxidases especially important for redox signaling;

to regulate NADPH oxidases in these conditions to provide the targeted therapeutic manipulation in a cell, tissue and/or pathway specific manner at appropriate points in the disease process;

co-administration with physiologically acceptable salts thereof Vitamin C exerts its effects indirectly via hypoxia-inducible factor, nitric oxide synthase and the heparan sulfate proteoglycan glypican-1, which is deglycanated in a vitamin C;

co-administration of L-arginine and vitamin C, to provides a synergistic action, which significantly augments the effectiveness of L-arginine, on nitric oxide bioavailability not seen by the compound alone; and improve platelet function in acute coronary syndrome and possibly reduce risk for coronary thrombosis.

DETAILED DESCRIPTION OF THE PREFERRED EMBODIMENTS

Figure 1:
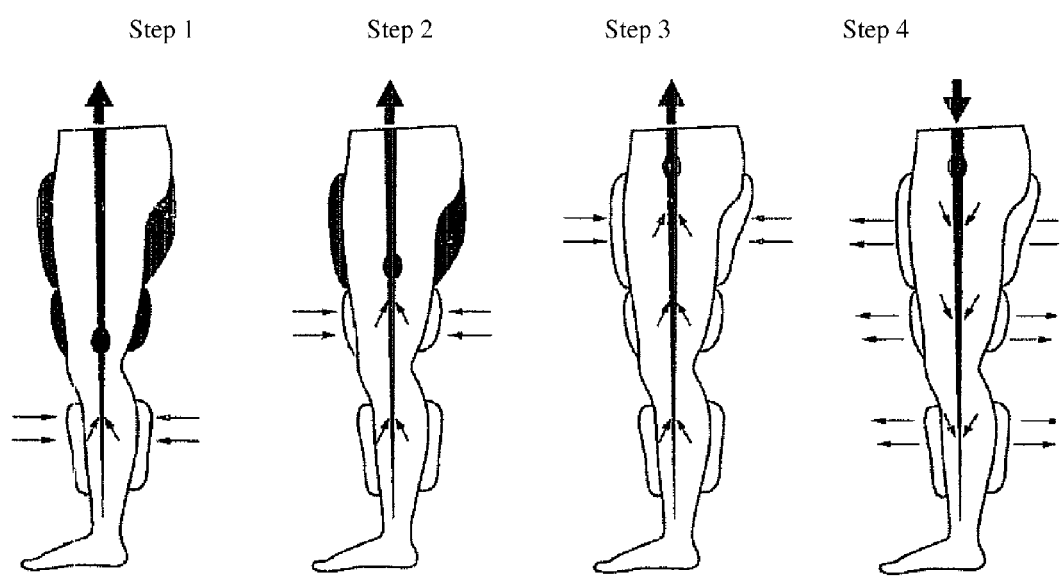
FIG. 1 depicts a prior external counter pulsation (ECP) device.

Referring now to the drawings, the system of the present invention is generally designated by the numeral 10. The system 10 includes a pumping assistant device 12 having pressure applicators, i.e., inflatable bladders with cuffs 14, 16, 18 and 20, fastened about the feet, calves, thighs and buttocks of a person and which are connected to a pneumatic device 22 that can be controlled by a microprocessor 24. In addition, there is provided an administration of compositions 26 which either directly or indirectly induce mediators for therapeutically treating the circulatory system. The microprocessor 24 is operably associated with sensors for sensing fluid dynamics within the circulatory system. Further, the microprocessor 24 is operably associated with software residing on memory which performs intelligent alterations of the pumping assistant device 12 as a function of the effect of administration of compositions 26 which is described herein.

The present invention is believed to improve on prior circulatory treatments which neglect combining a complete and dynamic pumping assistant device with administration of compositions which can increase the effect of mediators, such as nitric oxide production in the circulatory system. Nitric oxide generation can be enhanced due to the nature in which the venous plexus of the foot is activated and becomes one of the major sources of endothelial derived nitric oxide (NO) in the entire body. During ambulation the foot comes in contact with the ground for 60% of the time and the remaining 40% of the time is off of the ground, the swing time, the period in which the plantar venous plexus refills with venous blood before the next step is taken.

There is little direct pressure to the middle of the foot, all weight bearing takes place on the ball of the toes, the heel and lateral aspect of the plantar surface. The action of weight bearing (walking) causes the vessels of the plantar ach to be stretched and necked down in a milking action, forcing the blood to move forward into the larger venous conduits of the leg with great force. The stretching action or milking action of the venous plexus produces more shear stress on the endothelial lining of these vessels of the foot than in any other part of the body thus becoming a greater source of nitric oxide production than any other portion. It is estimated that the plexus can hold more than 50 cc of blood, which when activated is powerful enough to overcome a blood pressure cuff inflated to 100 mm Hg. dislocating a column of blood thru the venous conduits back to the heart.

Figure 2:
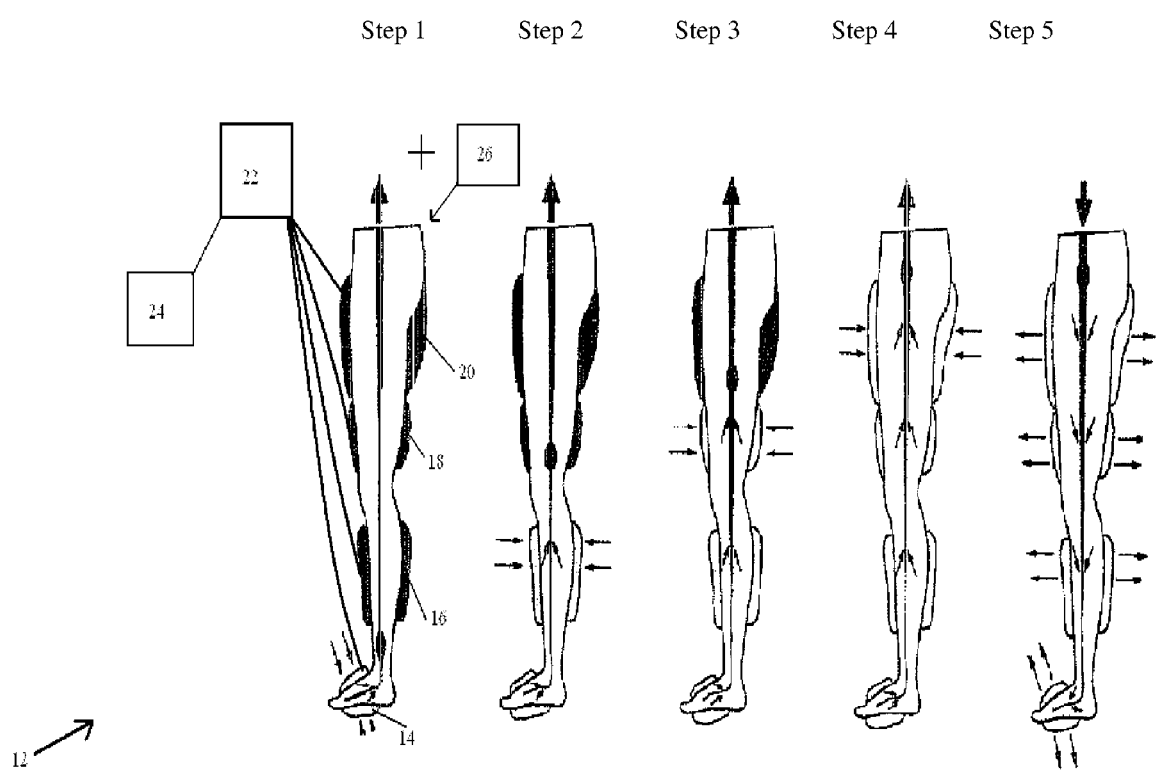
FIG. 2 depicts one version of the instant invention employing a modified pumping assistant device.

Conventional ECP devices alone all neglect the pumping of the plantar arch in the sole of the foot. The proposed new improved system 10 will replicate the act with the bladder 14 surrounding the foot inflating first. As shown in FIG. 2, these bladders 14, 16, 18 and 20 are sequentially inflated with air. First, the bladders 14 in the cuffs about the feet are inflated. About 30 to 50 milliseconds later, the bladders 16 in the cuffs about the calves are inflated, followed, after about 30 to 50 milliseconds, by inflation of the bladders 18 in the cuff about the thighs inflated, after about 30 to 50 milliseconds, by inflation of the bladders 20 in the cuff about the buttocks is inflated and deflation of the bladders 14, 16, 18 and 20 is initiated and terminated, respectively, during diastole, after the heart has finished its compression cycle (systole) and is temporarily at rest between compressions (heartbeats). Inflation to a desired pressure is begun after a selected time delay period from the "r" wave of the person's electrocardiogram (ECG), forcing blood up the arteries (and veins) to the heart, counter to the usual direction of arterial blood flow.

Compression of the bladders 14, 16, 18 and 20 continues for a selected time period, with simultaneous deflation of all of the bladders occurring during diastole, before the onset of systole, so as not to create resistance to the pumping of blood out of the left ventricle of the heart. When the bladders 14, 16, 18 and 20 deflate, the air is released into the atmosphere. Alternatively, the air may be withdrawn by the application of a vacuum to the bladders 14, 16, 18 and 20 if necessary.

Inflation of the bladders 14, 16, 18 and 20 tightens the cuffs thereof and forces blood from the feet, legs and buttocks up the veins into the right heart chambers (auricle and ventricle). This reduces the work-effort of the right heart, since a major portion of the heart's work is devoted to returning blood to the heart from the extremities. Inflation of the bladders also forces blood from the feet, legs and buttocks up the arteries toward the aorta.

Since the aortic valve, if competent, is closed during diastole, the blood cannot enter the
left heart chambers and flows from the aorta into the coronary, carotid and other arteries. An increase in intra-coronary artery pressure of up to 40% has been measured during compression, using tiny pressure transducers positioned in the coronary arteries of humans.
The repetitive application of the device has been shown to significantly increase intracoronary artery pressure while releasing endogenous (naturally occurring) angiogenic growth factors, resulting in the creation of capillaries and arterioles thru (angiogenesis) and restore vascular elasticity and vitality to the endothelial lining of the arteries of the heart, which occurs in the declining years of life.

To treat a chronic condition, such as stable angina pectoris (Angina) or Congestive Heart Failure (CHF), the system 10 is typically administered for a period of one hour, five days a week for seven weeks. It is thought that most or all of the angiogenic agents stored in the arteries is released within one hour by using the system 10, and delaying the treatment for a period of time gives the body time to manufacture and restock the depots in the arteries with such growth factors.

Associated with the microprocessor 24 is a control console, associated electronics and a touch-screen display, a power supply, one or more air compressors, an air reservoir and electrically actuated solenoid valves ("Solenoid Valves"), as known in the art, which are in fluid communication with and, when actuated, release air from the reservoir. Hoses attached to and in fluid communication with the outlets of the solenoid valves extend about four to six feet from the solenoid valves to bladders disposed in pockets within cuffs, which are fastened about the patient's feet, calves, thighs and buttocks.

The air compressor and solenoid valves associated with the system 10 may be mounted beneath the bed, or may be housed in a separate enclosure. Locating the air reservoir and attached solenoid valves beneath the bed shortens the length of the air hoses to the bladders 14, 16, 18 and 20 to about 2 to 3 feet, slightly reducing the inflation time of the bladders 14, 16, 18 and 20 and the amount of air lost from the hoses when deflated. Air pressure actuated valves ("APA Valves") can be attached directly to the individual inlets of bladders 14, 16, 18 and 20 disposed within pockets in the cuffs, which are fastened about the feet, calves, thighs and buttocks of the patient. An operating air pressure is maintained in a pneumatic trunk line that extends from a low pressure air reservoir (maintained at up to about 10 psi, preferably about 6 psi) and branches into smaller branch pneumatic lines connected to the APA Valves attached to the individual inlets of each of the bladders 14, 16, 18 and 20 within the cuffs.

The APA Valves, when actuated, admit air into the bladders 14, 16, 18 and 20 or allow air to escape through an exhaust port. The APA valves may be spool valves or any other type of valve known in the art. Air pilot lines are attached to, in fluid communication with, and extend from each of the solenoid valves, which are in fluid communication with a high pressure air reservoir (pressurized from about 12 to 30 psi, preferably about 15 to 26 psi). The air pilot lines extend to the APA Valves attached to the inlets of the bladders 14, 16, 18 and 20 disposed in the cuffs. By positioning the APA Valves at the inlets of each bladder 14, 16, 18 and 20, pressure is maintained at all times in the trunk and branch pneumatic supply lines. This minimizes the time of inflation of the bladders 14, 16, 18 and 20 and significantly reduces the amount of air lost during the exhaust cycle when the bladders are deflated, reducing the size and weight of the compressor(s), reservoir, and power supply. Actuating the APA valves attached directly to the bladders 14, 16, 18 and 20 of the cuffs with air pressure through the air pilot lines, instead of electrically, eliminates the risk of an electrical shock to the patient. The microprocessor 24 can be equipped with sensors, such as infrared sensors, to sense residual pressure and to control and set changes in pressure applied by means of tracking improvements peripheral blood flow with sensors distal and proximal to the pressure cuffs at each of the feet, calves, thighs and buttocks which provide feedback to the system 10 on improved circulation to increase or decrease pneumatic pressure. Thus, while under treatment with composition 26, the patient is monitored and the microprocessor 24 is equipped to control pressure according to when venous structure, such as the venous plexus, is full of blood. This can be determined as a function of the distal phase of an electrocardiogram. For example, the system 10 causes inflation bladders 14, 16, 18 and 20 when the respective venous structure is full to provide maximum effectiveness.

The pneumatic bladders 14, 16, 18 and 20 can be independently inflatable to independently controlled therapeutic pressures levels for independently controlled durations and periods of time by means of a plurality of air independently actionable valves. Each of the air actionable valves is engaged with one of the bladders 14, 16, 18 and 20, the air actionable valves are engaged in a manner to enable and inhibit air flow into the independent bladders 14, 16, 18 and 20.

Microprocessor 24 can be operably provided with means for selecting a direction of pressure applications on points of a patient's body including one of toward the heart and downward the feet of the patient. Microprocessor 24 is operably connected with means of releasing the therapeutic pressure before the inception of one of diastole or systole phase of heartbeat and can adjust pressure magnitudes and firing times based on the delay times from the "r" wave of the patient's electrocardiogram and duration in accordance with selected cardiac values. The system 10 via microprocessor 24 can select and automatically maintain a desired peak diastolic pressure to peak systolic pressure ratio by varying the therapeutic pressure magnitude in accordance with the patients peripheral blood flow and electrocardiogram data while selecting and automatically maintaining a desired peak diastolic pressure to peak systolic pressure ratio by varying the time of inception of therapeutic pressure application from the "r" wave of the electrocardiogram. Thus, the system 10 can select and automatically maintain a desired peak diastolic pressure to peak systolic pressure ratio by varying the duration of therapeutic pressure application.

The microprocessor 24 can increase minimum or maximum displayed "qrs" interval the applied pneumatic pressure to each bladder by means is a plurality of remotely actionable valves in electronic communication and controlled by the microprocessor 24 with the air reservoir and with each of the valves in fluid communication with one of air bladders cuffs attached to the various parts of the patient.

Composition 26 for treating circulatory ailments of the present invention is provided. The composition can be employed in conjunction with the device 12 for treating a patient susceptible to or suffering from a cardiovascular disorder or disease due the effects of the mediators C-reactive protein (CRP) and nicotinamide adenine dinucleotide phosphate-oxidase (NADPH) such as atherosclerosis, congestive heart failure, arterial stenosis, re-stenosis, smooth muscle cell hypertrophy, cardiac cell hypertrophy, thrombogenicity, clotting disorders, platelet disorders, myocardial infarction, cerebrovascular ischemia, peripheral vascular ischemia, angina pectoris or hypertension and other degenerative diseases. The present invention provides for composition 26 comprising a therapeutically effective combination of amounts and synergistic amounts of exogenous unfractionated Heparin, L-arginine, and L-arginine's supporting co-factor amino acids L-Citrulline, L-Norvaline, L-Orthinine and Nicotinamide Adenine Dinucleotide (NADH), as well as the independent free radical scavenger ascorbic acid, and the superoxide scavengers (4-hyroxy-2,2,26,6-tetramethylpiperidineNoxyl) Tempol, and Hydroxytyrosol, Apocynin (methoxy-substrated catechol) and folic acid, or physiologically acceptable salts or equivalents thereof which are used in the treatment and prevention of cardiovascular diseases and other degenerative disorders. The invention also provides for co-administration of L-arginine and vitamin C, wherein vitamin C provides a synergistic action, which significantly augments the effectiveness of L-arginine on nitric oxide bioavailability not seen by the compound alone. Vitamin C improves the acetylcholine stimulated forearm blood flow responses in patients with elevated CRP and coronary artery disease.

A therapeutically effective amount of heparin is provided in a patient in an amount ranging from about 10,000 IU to 200,000 IU daily, on variable schedule. The heparin is characterized such that it should be an amount sufficient to exert anti-thrombotic effects and less than an amount to cause hemorrhaging, while effectively maintaining integrity and functionality of the cellular membranes and surrounding environments.

A therapeutically effective amount of L-arginine range depends upon the underlying condition and nature of the physiological processes requiring treatment. The L-arginine should be a sufficient amount to sustain a level of nitric oxide to keep various cell types from dysfunctional activation states in the patient, to increase prostacyclin secretion, to reduce secretion of extra-cellular proteins and heparin binding proteins, and to bind to available sulfate and carboxyl groups on heparin in order to increase extra-cellular matrix barrier properties which in turn decrease extra-cellular matrix pore size and permeability. Exemplary dosage amount of L-arginine ranges from about 1,500 mg to 20,000 mg daily and can be added together with L-citrulline, L-ornithine, L-Norvaline and nicotinamide adenine dinucleotide hydrogen or separately from the L-arginine. Like L-arginine and L-ornithine, L-citrulline is a metabolite in the urea cycle and is involved in liver detoxification (the source of C-reactive protein), it is also critical in the vasodilation pathway. When endogenous supplies of ornithine carbarmoyltransferase are insufficient as in the case of many cardiovascular conditions, supplemental L-citrulline supports ammonia incorporation and liver detoxification of ammonia.

In turn, this supports the production of Nitric Oxide by sparing L-arginine. L-norvaline is a strong inhibitor of arginase activity because of its similarity to ornithine, causing a feedback on the activity of arginase. When arginase is inhibited, NO is produced more continuously at a higher rate in the presence of NOS and adequate L-arginine. L-arginine is the limiting factor in the production of NO from NOS. Inhibiting the arginase enzyme effectively increases the production of NO by as much as 60%. NADH (nicotinamide adenine dinucleotide hydrogen) is added as this molecule is an energy source. A therapeutically effective amount of amino acids range depends upon the underlying condition and nature of the physiological processes requiring treatment. For example, dosage ranges are for L-citrulline 100 mg to 3 000 nig daily, L-norvaline 100 mg to 3000 mg daily, L-orthinine 100 mg to 1000 mg daily, NADH 5 to 10 mg daily. Individual physiological condition plus the weight, age, disease, sex of the patient will largely dictate the required dosages and frequencies of arginine and its co-factor administration.

The compound of the present invention can be formulated for oral, sublingual, subcutaneous, intravenous, transdermal or rectal administrations in dosages and in admixture with pharmaceutical excipients or vehicles including implantation or controlled-release devices. All of these components in the invention comprised of unfractionated heparin, L-arginine, L-arginine's co-factor amino acids (L-citrulline, L-norvaline and nicotinamide adenine dinucleotide (NADH), as well as the independent free radical scavenger ascorbic acid, and the superoxide scavengers (4-hyroxy-2,2,26,6-tetramethylpiperidine-N-oxyl) Tempol, and hydroxytyrosol, apocynin (medioxy-substrated catechol) and folic acid, or physiologically acceptable salts or equivalents thereof or functional analogs or physiologically acceptable salts thereof can be dispensed in a non-toxic liquid vehicle, such as water. Alternatively, the compound can be given in tablet, capsule, powder, granules or coated tablet form. The compound can be made in a conventional manner, and may be mixed with conventional pharmaceutical auxiliaries, such as binders, fillers, preservatives, tablet disintegrators, flow regulators, plasticizers, wetting agents, dispersants, emulsifiers, solvents, retarding agents and/or anti-oxidants. It also can be contained or complexed with lipids in various formulations and molecular arrangements, e.g. lipid tubules.

An efficiently operating homeostatic system is crucial to cellular function within mammalian organisms. In a healthy state, there is formed a gel matrix of heparin, arginine and water polymers, which houses a plurality of other molecules by accommodating dynamic binding of and release of such molecules without reaching concentration levels which destroy the gel structure and its regulatory functionalities.

Commercially, heparin is normally derived from animal tissue such as livers and lungs of cattle, bovine species and sheep. Polymer strands are an organizing determinant for membranes, proteins, receptors, ion channels, cell organelles, nuclear membranes, membrane pores, and other complex cellular constituents. The polymers organize water into arenas for confining bilipid layer membranes, for example, creating cell turgor and form and limiting hydrolytic properties of water on other molecular structures.

Heparin's high sulfate content imparts a high negative charge which attracts and binds positively charged substances like basic amino acids, basic domains of proteins and peptides, cations, water and other such charged molecules. Arginine has a high positive charge and strongly associates with heparin along membrane surfaces such as endothelium and basement membranes and in association with water, organize as gel matrix. The gel may be in a constant state of change, including transitions from one state or phase to another. As such, conformation can change and derangements occur as different substances move in and out of the gel and as the gel properties change. A healthy gel matrix is formed from endogenous heparin, endogenous arginine and water when protected from the effects of C-reactive protein (CRP) and nicotinamide adenine dinucleotide phosphate-oxidase-NAD(P)H.

The health gel structure has a conformation that preferentially supports interaction and binding of foreign molecules. The capacity to accommodate intrusions of such molecules before the gel structure collapses and hoses its functionality is an important characteristic of the gel system.

The polar molecules that heparin binds and inactivates thereby modulating their activity, are serine proteases, other clotting factors and thrombolytic agents, antithrombin-thrombin, complement, apo-lipoproteins, growth-promoting factors, mitogens, heparinase, lipoprotein lipase, growth-inhibiting factors, chemotactic factors, super oxide dismutase, cytokines, numerous enzymes, and cytoskeletal proteins such as fibronectin. As these intrusions accumulate locally or in a distributed fashion, they cause an interference within the gellular association of heparin and arginine. The interference can cause the gel structure to deteriorate, thus increasing its porosity or collapse altogether in a localized or distributed fashion. In addition, the intrusion may trigger a release of other bound polar molecules, such as calcium which would induce a non-homeostatic event.

These intrusions result in a displacement of arginine and decreased generation of nitric oxide as an additional effect. Intrusions limit the binding capacity of the heparin for arginine and other molecules within the gel.

In order to reverse this disruption of the gel matrix caused by removal of arginine and/or heparin, the present invention employs a composition to maintain and rejuvenate the gel matrix and its functionality. In this regard, the present invention utilizes a full range of molecular weight heparin and arginine to give optimal pore closure and stabilization, and number and distribution of binding sites, wherein signaling, anti-proliferation, anti-thrombotic, anti-coagulant properties are maintained. Thus, the homeostasis-promoting functionalities of heparin, arginine, and heparin-arginine-water gel matrix, resultant from the herein-described composition, retard continuous and accumulative injury to cellular domains. By this retarding effect, cholesterol accumulations, generally referred to as "arterial plaques" are minimized. Heparin and arginine co-administration also leads to increased lipoprotein and lipase release wide beneficial effects on plaque stability, growth, rupture, and regression.

The expression of endogenous heparin is surface receptor dependent in that the prostacyclin, in association with heparin at the gel surface, generates a signal to the golgi apparatus to produce endogenous heparin. Added exogenous heparin accumulates at the blood/endothelium surface thereby reconstituting the prostacyclin receptors which may have been damaged and depleted over time. Nitric oxide production at or near the same surface occurs from nitric oxide synthase action on exogenous and endogenous arginine substrate. This nitric oxide amplifies the signal by increasing the local concentration of prostacyclin, whose production is mediated by the nitric oxide.

Thus, heparin is generated in quantities sufficient to allow reassociation of arginine and heparin and restore the gel structure, as well as releasing or rearranging potentially injurious molecules in the gel matrix. Addition of heparin to the gel system protects the functionality of the arginine in the gel, and addition of arginine to the gel system protects the functionality of heparin in the gel. In the extragellular medium, the ability of heparin to bind and quiesce molecules is augmented by simultaneous addition of exogenous heparin and exogenous arginine, wherein exogenous heparin is binding to extragellular potentially-intruding molecules, thus allowing existing gellular heparin to associate with gellular arginine. Exogenous arginine becomes the more available substrate for nitric oxide synthase, thereby protecting gellular endogenous arginine from the nitric oxide synthase activity and allowing die endogenous arginine to continuously re-associate with the gellular heparin, thus protecting the gel functionality.

The binding of water, small anions and cations within the heparin-arginine-water gel is facilitated by pi-bonding properties inherent in the saccharide ring structure within the heparin polymers. Changes in the shared electron density and electrical charge variation regulate the state of solvation and conformation of the gel polymers. Thus, small anion and cation binding induces changes in the state of solvation, changes in catalytic and hydrolytic properties of water, and changes in capacity of the gel to bind water and other molecules.

Heparin, via its association with arginine, and arginine's cofactor amino acids enhances regeneration of dysfunctional endothelium following an injury to an endothelium surface, the molecular cascade of events precipitated by mediators C-reactive protein (CRP) and nicotinamide adenine dinucleotide phosphate-oxidase (NADPH) require the specific medicinal effects of the dependent free radical scavenger ascorbic acid, and the superoxide scavengers (4-hyroxy-2,2,26,6-tetraniethylpiperidine-N-oxyl) Tempol and Hydroxytyrosol, Apocynin (medioxy-substrated catechol) and folic acid.

Although nitric oxide of endothelial origin plays a major role in warding off inappropriate thrombus formation, platelets also express the "constitutive" isoform of nitric oxide synthase (cNOS). Activation of this enzyme by calcium influx during platelet aggregation provides an important feedback signal that dampens platelet recruitment. Platelets also express a membrane-bound NAD(P)H oxidase complex, activated by collagen receptors, that produces superoxide. Superoxide can directly quench NO; moreover, by giving rise to peroxynitrite, it can oxidize the cNOS cofactor tetraliydrobiopterin (BH4), thereby suppressing cNOS activity and converting it to superoxide generator.

In a canine model of acute coronary syndrome, infusion of BH4 has been shown to prevent thrombus formation. Platelets from patients with acute coronary syndrome produce markedly less NO than do control platelets. A reasonable explanation for these findings is that episodic contact with collagen boosts platelet superoxide production, oxidizing BH4. Since 5-methyltetrahydrofolate can reduce oxidized BH4, or otherwise compensate for its deficiency, supplementation with its precursor folic acid improves platelet function in acute coronary syndrome and possibly reduce risk for coronary thrombosis in other at-risk patients. It is thought that superoxide production is increased, and nitric oxide production diminished, in platelets of diabetics; the ability of glutathione—a peroxynitrite scavenger—to largely ameliorate these abnormalities, is consistent with a prominent role for BH4 deficiency in diabetic platelet malfunction. Reports that platelet NO production is decreased, and/or superoxide production increased, in patients with disorders associated with insulin resistance syndrome, suggest that BH4 deficiency is potentially remediable with high-dose folate may likewise contribute to the platelet hyperreactivity noted in these disorders. Supplements of vitamin C and L-arginine releases the bioavailable NO held in tissues while boosting the platelet production of NO. These nutrients in appropriate doses act directly on platelets to further diminish risk for thrombotic episodes.

Hydroxytyrosol (10 micro M) efficiently protected the aorta against the CRP-induced impairment of the NO(*)-mediated relaxation (P<0.05). Oleuropein, tyrosol, mid homovanillic alcohol, major metabolites of hydroxytyrosol, do not show protection. Moreover, hydroxytyrosol is a potent OH(*) scavenger, which can be attributed to its catechol moiety. Because of its amphiphilic characteristics (octanol-water partitioning coefficient=1.1), hydroxytyrosol will readily cross membranes and provide protection in the cytosol and membranes, including the water-lipid interface.

Since CRP inhibits endothelium-dependent NO-mediated dilation of coronary arterioles by increasing vascular superoxide production, therapies which directly affect the production of CPR become essential in controlling key vascular signaling molecules in oxidative stress such as, distinct superoxide-generating enzymes and stress-activated protein kinases that are involved in the CRP-mediated effect.

The present invention provides a formulation for treating a patient susceptible to or suffering from a cardiovascular disorder or degenerative diseases and more particularly, but not by way of limitation, to a formulation for preventing and treating the affects of cardiovascular mediators C-reactive protein (CRP) and nicotinamide adenine dinucleotide phosphate-oxidase-NADPH) in atherosclerosis, congestive heart failure, arterial stenosis, re-stenosis, smooth muscle cell hypertrophy, cardiac cell hypertrophy, thrombogenicity, clotting disorders, platelet disorders, myocardial infarction, cerebrovascular ischemia, peripheral vascular ischemia, angina pectoris or hypertension.

An example of the composition of the invention used over a twelve month period as compared to conventional treatment consisting of one hundred and twenty-five for patients suffering from unstable angina is as follows:

| Therapy Results | Conventional | Instant Invention Composition Oral |
|---|---|---|
| Acute Myocardial Infarction | 28% | <1% |
| Death Without Procedures | 25% | <1% |
| Death With Procedures | 3-7% | zero |
| CABG or PTCA | 50% | <3% |
| CVA rate with severe carotid ulceration and/or stenosis: | 25% | <1% |
| Death from congestive Heart failure | 30% | <5% |
| Recurrent hospitalizations | Common | Rare |

Therapy Responses

The arginine and heparin therapy has been used with over 1400 patients who have been directly observed to produce the following clinical responses:

Resolution of hypertension, Dramatic decreases in serum lipids, Dramatic increase in serum HDL, Resolution of primary thrombocytosis, Resolution of pulmonary hypertension, Improvement in vascular stenosis, Improvement in vascular insufficiency, Resolution of claudication, Resolution of ischemic foot ulcerations, Resolution of DVT without secondary venous insufficiency, Resolution vertebrobasilar insufficiency, and Regression of atherosclerotic plaque formation.

Case Example Mrs. L R

Developed Transient Ischemic Attack (TIA) symptoms in both the middle cerebral and posterior circulations and underwent a cerebral arteriogram resulting in findings of severe stenosis with ulceration of left internal carotid artery, 50-70% left vertebral stenosis, and total occlusion of right vertebral artery. The patient was not on therapy prior to event.

After a carotid endarterectomy, the present invention therapy began to prevent post surgical occlusion of left carotid and to protect the uninvolved left vertebral artery. Follow-up carotid-vertebral ultrasound at three months showed no restenosis. More importantly, the previously totally occluded right vertebral artery was fully patent with normal flow velocities.

The recent finding concerning the importance of patency in occluded arteries following acute myocardial infarction, plus the knowledge that coronary arteries remote from active plaque sites demonstrate reduced vasoactive potential as well as flow volumes with increased thrombogenic potential, leads to the belief that patency of CVA-occluded arteries will similarly be found important in long-term outcome for intra and extracranial CVA patients. The inventor who suffered a CVA on Aug. 11, 2001 credits his rather dramatic recover to the therapy.

It is clear that the stenosis is caused by the endothelial derangements, and that restoration of endothelial functional integrity leads to improvement and/or resolution of the stenosis itself and the fallacy of dealing with isolated stenosis in arteries. Unfortunately, plaque stability cannot currently be measured or quantified except in extremes.

Case J. O.

This 53-year-old male with hypertension and hypercholesterolemia had classic symptoms of Transient Cerebral Ischemia with episodic arm dysesthesia, mentation changes, vertigo, and hand weakness, which evolved over a period of months. A carotid ultrasound demonstrated luminal irregularity with flow reversal and endothelial ulceration in the orifice of the carotid artery. Treatment was initiated according to the previously outlined protocol. Within 60 days the frequency of symptoms significantly decreased, the hypertension was controlled well for the first time in years, and the mentation changes abated.

At 90 days the carotid ultrasound was repeated with the following findings:

luminal irregularity was entirely resolved endothelial ulceration was absent flow reversal observed adjacent to the areas of ulceration was resolved The patient remained asymptomatic after 7 months of treatment Case B. H.:

This man in his 50's, unstable angina with 90% left coronary artery stenosis and 50% mid right coronary stenosis. The results of two coronary angioplasties of the mid left lesion were insignificant in resolving his chest pain. The first relieved his symptoms for 6 months; the second for 3 months. Coronary bypass surgery was recommended.

Following the outlined treatment with the invention for 4 months he could exercise for 30 minutes without angina.

Because of his asymptomatic condition following treatment, he elected to discontinue the treatment without consultation with the inventor. Within 3 weeks his symptoms recurred and he developed a total occlusion not of the more severe left coronary lesion, but of the previous 50% mid-right lesion. Thrombolytic therapy was administered with minimal myocardial damage occurring despite 2-3 days of continuous chest pain.

Again coronary bypass surgery was recommended after a repeat arteriogram showed 95+% occlusion of the mid right coronary artery.

The patient resumed treatment with nearly complete resolutions of symptoms for 7 months. Intermittent chest discomfort began recurring after increased prednisone dosage was instituted for his lupus erythematosis arthritis. Because of concern for the possibility of acute total occlusion of the now 95% right lesion, a repeat arteriogram was performed with the following results:

The 90% left coronary lesion has regressed to 50% significantly and the area subtended by that artery has been supplied by innumerable collateral arteries some of which are as large as native branch coronary arteries.

The 95% right coronary stenosis has progressed to total occlusion in the intervening months, yet there is essentially no decrease in inferior wall motion as would be expected from total occlusion. There have been generated in the interval form the most recent arteriogram huge collateral arteries. These are of sufficient size that the cardiologist performing the current arteriogram misinterpreted these as being native arteries supplying the Right Coronary distribution. The patient was told that all the plaque involving the Right Coronary was resolved. Only by comparison with the previous arteriogram was the occlusion of the true-native artery identified.

Coronary bypass surgery is not felt indicated in the face of resolution of luxurious antegrade and retrograde-collateral perfusion in the right coronary bed and regression with "auto-bypass" via collaterals of the previously problematic proximal 90% left coronary lesion. The area of previous infarction has essentially normal myocardial contractility despite the prolonged ischemic insult prior to the thrombolytic therapy.

The collateral artery formation is clearly accelerated by the treatment. The lack of significant myocardial contractility defect following days of ischemia and subsequent total occlusion is clear evidence of the treatment's residual capacity for stabilization of cell membranes despite a 3-week period off the treatment.

The invention is not limited by the embodiments described above which are presented as examples only but can be applied and modified in various ways within the scope of protection defined by the appended patent claims.

What is claimed is:

1. A controlling system comprising:
   a pumping assistant device having pressure applicator inflatable cuffs adapted to be fastened about feet, calves and thighs of a person and which are connected to a pneumatic device;
   a regimen of compositions which either directly or indirectly induce mediators for therapeutically treating the circulatory system of the person, wherein said compositions include a therapeutically effective combination of amounts and synergistic amounts of exogenous unfractionated Heparin, L-arginine, and L-arginine's supporting co-factor amino acids L-Citrulline, L-Norvaline, L-Orthinine and Nicotinamide Adenine Dinucleotide (NADH), as well as independent free radical scavenger ascorbic acid, and superoxide scavengers Tempol (4-hyroxy-2,2,26,6-tetramethylpiperidine-N-oxyl), and Hydroxytyrosol, Apocynin (methoxy-substrated catechol) and folic acid, or physiologically acceptable salts thereof which are used in the treatment and prevention of cardiovascular diseases and degenerative disorders;
   a microprocessor operably connected to said pumping assistant device for control thereof, wherein said microprocessor has operably connected to infrared sensors disposed on the person for sensing residual pressure and providing said microprocessor control to set changes in pressure applied through said pumping assistant device by tracking improvements in peripheral blood flow with said sensors distal and proximal to said pressure applicator inflatable cuffs at each of the feet, calves, thighs and buttocks which provide feedback to said microprocessor on improved circulation; and
   wherein said microprocessor is operably associated with a software residing on a memory which performs intelligent alterations of said pumping assistant device as a function of an effect of administration of compositions which either directly or indirectly induce mediators for therapeutically treating the circulatory system of the person to increase or decrease pneumatic pressure accordingly in a direction and selecting a direction of applying therapeutic pressure applications on points of a patient's body including one of toward the heart and downward toward the feet of the patient and releasing the therapeutic pressure before inception of one of diastole or systole phase of heartbeat and adjusting pressure magnitudes and firing times based on delay times from the "r" wave of the patient's electrocardiogram and duration in accordance with selected cardiac values.

2. The controlling system of claim 1, wherein said software automatically maintains a desired peak diastolic pressure to peak systolic pressure ratio by varying therapeutic pressure magnitude in accordance with a patient's peripheral blood flow and electrocardiogram data while selecting and automatically maintaining a desired peak diastolic pressure to peak systolic pressure ratio by varying time of inception of therapeutic pressure application from the "r" wave of electrocardiogram data.

3. The controlling system of claim 2, wherein said software automatically maintains a desired peak diastolic pressure to peak systolic pressure ratio by varying the duration of therapeutic pressure application and means for adjusting minimum and maximum displayed "qrs" interval the applied pneumatic pressure to a part of the patient.

4. The controlling system of claim 3, wherein said pressure applicator inflatable cuffs are independently inflatable to independent therapeutic pressures levels for independently selected durations and periods of time by a plurality of independently actionable valves, each of the actionable valves engaged with one of said pressure applicator inflatable cuffs, said actionable valves are engaged in a manner to enable and inhibit air flow into said independent applicator inflatable cuffs.

5. The controlling system of claim 4, wherein said system includes a high pressure source in communication with said plurality of actionable valves enabling a lower air pressure source in communication with the corresponding applicator inflatable cuffs for inflation and deflation.

6. The controlling system of claim 1, wherein said system further includes co-administration of L-arginine and vitamin C.

* * * * *